US010583077B2

(12) United States Patent
Lange et al.

(10) Patent No.: US 10,583,077 B2
(45) Date of Patent: Mar. 10, 2020

(54) PRODUCT AND METHOD FOR THE TEMPORARY SHAPING OF KERATIN-CONTAINING FIBERS

(71) Applicant: Henkel AG & Co. KGaA, Duesseldorf (DE)

(72) Inventors: Julia Bibiane Lange, Bad Bramstedt (DE); Anna Puls, Winsen (DE); Cyrielle Martinez, Hamburg (DE); Bernd Richters, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/555,975

(22) PCT Filed: Nov. 11, 2015

(86) PCT No.: PCT/EP2015/076326
§ 371 (c)(1),
(2) Date: Sep. 6, 2017

(87) PCT Pub. No.: WO2016/142010
PCT Pub. Date: Sep. 15, 2016

(65) Prior Publication Data
US 2018/0055755 A1 Mar. 1, 2018

(30) Foreign Application Priority Data
Mar. 9, 2015 (DE) .................. 10 2015 204 149

(51) Int. Cl.
*A61K 8/81* (2006.01)
*A61Q 5/06* (2006.01)
*A61K 8/41* (2006.01)

(52) U.S. Cl.
CPC ............. *A61K 8/8152* (2013.01); *A61K 8/41* (2013.01); *A61K 8/8147* (2013.01); *A61K 8/8176* (2013.01); *A61K 8/8182* (2013.01); *A61Q 5/06* (2013.01); *A61K 2800/594* (2013.01)

(58) Field of Classification Search
CPC .. A61K 2800/594; A61K 8/41; A61K 8/8147; A61K 8/8152; A61K 8/8176; A61K 8/8182; A61Q 5/06
See application file for complete search history.

(56) References Cited

U.S. PATENT DOCUMENTS

| 6,190,647 | B1 | 2/2001 | Karlen et al. | |
|---|---|---|---|---|
| 2007/0224145 | A1* | 9/2007 | Walter | A61K 8/25 424/70.6 |
| 2011/0135589 | A1 | 6/2011 | Knappe et al. | |
| 2014/0093467 | A1* | 4/2014 | Knappe | A61K 8/8152 424/70.15 |
| 2018/0049967 | A1* | 2/2018 | Lange | A61Q 5/06 |
| 2018/0055756 | A1* | 3/2018 | Lange | A61Q 5/06 |
| 2018/0168989 | A1* | 6/2018 | Lange | A61K 8/8152 |

FOREIGN PATENT DOCUMENTS

| DE | 102007008089 | A1 | 8/2008 | |
|---|---|---|---|---|
| DE | 102011077364 | * | 11/2011 | ............... A61K 8/81 |
| DE | 102013225753 | A1 | 5/2014 | |
| EP | 1238646 | A1 | 9/2002 | |
| EP | 1878423 | A2 | 1/2008 | |
| WO | WO2013/072118 | * | 5/2013 | |

OTHER PUBLICATIONS

Dow Personal Care Portfolio (http://www.kalekimya.com/admin/hizmetler_dokuman/1427398856_Dow_Portfolio_for_Personal_Care.pdf 2014) (Year: 2014).*
Signori, V., "Cosmetic and science Technology, Acrylates copolymers—Why do we need to neutralize them", Jan. 1, 2006, 219.
Jones, C., "Multifunctional Synthetic Rheology Modifiers for Personal Care Formulations: More Than Just Thickeners", May 1, 2005, 1-23.
BASF, "Acrylic terpolymer products for hair-setting preparations with a strong, long-lasting effect (Luvimer)", Sep. 1, 2000, 1-21.
EPO, International Search Report and Written Opinion issued in International Application No. PCT/EP2015/076326, dated Jan. 7, 2016.

* cited by examiner

*Primary Examiner* — Anna R Falkowitz
(74) *Attorney, Agent, or Firm* — Lorenz & Kopf, LLP

(57) ABSTRACT

The disclosure relates to a cosmetic composition for the temporary shaping of hair, containing a combination of two specific anionic acrylate copolymers. The cosmetic composition provides an extremely good moisture resistance.

15 Claims, No Drawings

PRODUCT AND METHOD FOR THE TEMPORARY SHAPING OF KERATIN-CONTAINING FIBERS

CROSS-REFERENCE TO RELATED APPLICATION

This application is a U.S. National-Stage entry under 35 U.S.C. § 371 based on International Application No. PCT/EP2015/076326, filed Nov. 11, 2015 which was published under PCT Article 21(2) and which claims priority to German Application No. 102015204149.2, filed Mar. 9, 2015, which are all hereby incorporated in their entirety by reference.

TECHNICAL FIELD

The present disclosure relates to a cosmetic composition for hair setting or respectively the temporary shaping of keratinous fibers, especially human hair, wherein the composition contains a combination of two anionic acrylic polymers.

BACKGROUND

The temporary formation of hairstyles for a longer period of time up to several days generally requires the use of stabilizing active substances. Therefore, hair treatment products, which temporarily shape hair, play an important role. Corresponding means for temporary shaping usually contain synthetic polymers and/or waxes as stabilizing active substances. Means to support temporary shaping of keratinous fibers can be prepared as hairspray, hair wax, hair gel and hair foam, for example.

The most important property of a medium for temporary shaping of hair—also referred to below as a styling product—consists of giving the treated fibers as strong a hold as possible in the newly shaped form, i.e. a shape imposed on the hair. This is also referred to as long-lasting styling or a high degree of hold for the styling product. Long-lasting styling is essentially determined by the type and quantity of the stabilizing active substances used, but the other constituents of the styling product can also have an influence.

Along with a high degree of hold, styling products must meet a whole series of additional requirements. These can be roughly subdivided as the properties of hair and of the respective formulation, such as the properties of the foam, gel or sprayed aerosol, and properties which affect the handling of the styling product, wherein the hair properties are assumed particular importance. Moisture resistance, low tack and a balanced conditioning effect are especially to be noted. Furthermore, a styling product should be as universally applicable as possible for all types of hair and be gentle on hair and skin.

To satisfy the various requirements a multitude of synthetic polymers have been developed as stabilizing active substances used in styling products. The polymers can be classified as cationic, anionic, nonionic and amphoteric stabilizing polymers. When the polymers are used on hair, ideally a polymer film results which gives the hairstyle a strong hold while at the same time being sufficiently flexible so as not to break under stress. If the polymer film is fragile, film plaque or residues form which separate during movement of the hair and give the impression that the user of the corresponding styling product has dandruff. Similar problems result if waxes are used as a stabilizing active substance in the styling product. If the styling product is a gel or a paste, the polymers should also have thickening properties.

Known anionic polymers used in hair setting products are acrylate copolymers with two or more structural units. The German application DE 10 2007 053 954 A1 describes particular copolymers of this type with the trade name Aculyn® 33A (INCI: acrylates copolymer) and their use in cosmetic compositions for temporary shaping of keratinous fibers.

Furthermore, hydrophobic modified acrylate copolymers (INCI: acrylates copolymer (and) water) are available commercially; these essentially act as thickening agents. The datasheet for AquaStyle® SH-100 Polymer (from Ashland Inc.) describes such an acrylate copolymer and its use in combination with carbomers. Suitability for crystal-clear hair gels, good initial stiffness, moisture resistance and long-term action are described.

An object as contemplated herein was to make additional suitable polymer combinations available which are distinguished by good film formation and/or stabilizing properties and have a very high degree of hold without sacrificing flexibility and good moisture resistance—particularly resistance to sweat and water—and which are also suited for manufacturing stable viscous compositions as well as stable, transparent cosmetic compositions. Currently available styling products are still especially able to be improved in that regard, as a good combination of stiffness and high humidity curl retention is not always sufficiently ensured. Therefore, it is an object as contemplated herein to provide styling products of this type, which alongside the aforementioned properties particularly resulted in good stiffness as well as high humidity curl retention.

BRIEF SUMMARY

A cosmetic composition for temporary shaping of keratinous fibers is provided herein. The cosmetic composition includes at least one acrylate copolymer (a). The at least one acrylate copolymer (a) is comprised of at least the following monomer units: (a1) at least one (meth)acrylic acid unit and (a2) at least one (meth)acrylic acid ester unit. The cosmetic composition includes further includes at least one anionic acrylate copolymer (b). The at least one anionic acrylate copolymer (b) is comprised of at least the following monomer units: (b1) at least one (meth)acrylic acid unit, (b2) at least one (meth)acrylic acid ethyl ester unit, and (b3) at least one (meth)acrylic acid ester unit which is different from the (meth)acrylic acid ester unit (b2) and which has a hydrophobic group as an ester group.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

As contemplated herein, this was achieved by a combination of two particular anionic acrylate polymers, which differ from one another.

The following are provided by the present disclosure:
1. A cosmetic composition for temporary shaping of keratinous fibers, which contains:
   (a) at least one acrylate copolymer (a) which is comprised of at least the following monomer units:
   (a1) at least one (meth)acrylic acid unit
   (a2) at least one (meth)acrylic acid ester unit
   and
   (b) at least one anionic acrylate copolymer (b) which is different from the acrylate copolymer (a) and which is comprised of at least the following monomer units:
   (b1) at least one (meth)acrylic acid unit
   (b2) at least one (meth)acrylic acid ethyl ester unit
   (b3) at least one (meth)acrylic acid ester unit which is different from the (meth)acrylic acid ester unit (b2) and which has a hydrophobic group as an ester group.
2. The cosmetic composition according to Point 1, wherein the at least one acrylate copolymer (a) is comprised of the monomer units (a1) (meth)acrylic acid and (a2) (meth)acrylic acid ester, with reference to its total weight to at least about 90 weight percent, preferably to at least about 95 weight percent and especially to at least about 97 weight percent.
3. The cosmetic composition according to one of the preceding points, wherein the acrylate copolymer (a) has an acrylic acid ester unit, preferably an acrylic acid (C1-4)-alkyl ester as a monomer unit (a2).
4. The cosmetic composition according to one of the preceding points, wherein the composition contains the copolymer (a) in a proportion of from about 0.05 to about 5.0 weight percent, preferably from about 0.5 to about 4.0 weight percent, and more preferably from about 1.0 to about 3.0 weight percent with reference to the total weight of the cosmetic composition.
5. The cosmetic composition according to one of the preceding points, wherein the anionic acrylate copolymer (b) has methacrylic acid as a monomer unit (b1) and ethyl acrylate as a monomer unit (b2).
6. The cosmetic composition according to one of the preceding points, wherein the anionic acrylate copolymer (b) has a (meth)acrylic acid alkyl ester as a monomer unit (b3).
7. The cosmetic composition according to one of the preceding points, wherein the composition contains the anionic acrylate copolymer (b) in a proportion of from about 0.05 to about 5.0 weight percent, preferably from about 0.5 to about 4.0 weight percent, and more preferably from about 1.0 to about 3.0 weight percent with reference to the total weight of the cosmetic composition.
8. The cosmetic composition according to one of the preceding points, wherein the anionic acrylate copolymer (b) has a viscosity of from about 60,000 to about 120,000 cPs at a solids content of 2 weight percent in an aqueous neutralized solution at 25° C.
9. The cosmetic composition according to one of the preceding points, wherein the anionic acrylate copolymer (a) is one with the INCI designation "acrylates copolymer", in particular Aculyn® 33A (from Rohm&Haas).
10. The cosmetic composition according to one of the preceding points, wherein the anionic acrylate copolymer (b) is one with the INCI designation "acrylates copolymer (and) water", in particular AquaStyle SH-100 (from Ashland Inc.).
11. The cosmetic composition according to one of the preceding points, wherein the anionic acrylate copolymer (a) is one with the INCI designation "acrylates copolymer" and the anionic acrylate copolymer (b) is one with the INCI designation "acrylates copolymer (and) water".
12. The cosmetic composition according to one of the preceding points, wherein the anionic acrylate copolymer (a) is Aculyn® 33A (from Rohm&Haas) and the anionic acrylate copolymer (b) is AquaStyle® SH-100 (from Ashland Inc.).
13. The cosmetic composition according to one of the preceding points, which, with reference to the total weight of the cosmetic composition, contains:
   from about 0.05 to about 5.0 weight percent of the anionic acrylate copolymer (a) and
   from about 0.05 to about 5.0 weight percent of the anionic acrylate copolymer (b).
14. The cosmetic composition according to one of the preceding points, containing, with reference to the total weight of the cosmetic composition:
   from about 1.0 to about 3.0 weight percent of the anionic acrylate copolymer (a) and
   from about 1.0 to about 3.0 weight percent of the anionic acrylate copolymer (b).
15. The cosmetic composition according to one of the preceding points, wherein the composition also contains at least one polymer (c) differing from the acrylate copolymers (a) and (b), in particular an anionic or non-ionic polymer (c).
16. The cosmetic composition according to one of the preceding points, characterized in that, with reference to its total weight, it also
   c) contains from about 1.0 to about 10 weight percent polyvinyl pyrrolidone and/or vinyl pyrrolidone/vinyl acetate copolymer, preferably polyvinyl pyrrolidone.
17. The cosmetic composition according to Point 16, characterized in that the weight fraction of the polyvinyl pyrrolidone and/or vinyl pyrrolidone/vinyl acetate copolymer c) comprises from about 2.0 to about 8.5 of the total weight of the cosmetic composition, preferably from about 3.0 to about 7.0 weight percent.
18. The cosmetic composition according to one of the preceding points, wherein the composition contains water in a proportion of from about 50 to about 95 weight percent, preferably between about 60 and about 90 weight percent and in particular between about 65 and about 85 weight percent with reference to the total weight of the cosmetic composition.
19. The cosmetic composition according to one of the preceding points, wherein the composition is present as a hair gel, hairspray, hair foam or hair wax, in particular as a hair gel.
20. A use of a cosmetic composition according to one of the points 1 to 19 for temporary shaping of keratinous fibers.
21. The use of a cosmetic composition according to one of the points 1 to 19 for improving the moisture resistance of temporarily shaped keratinous fibers.
22. A method for temporary shaping of keratinous fibers, in particular human hair, wherein the cosmetic composition is applied to keratinous fibers according to one of the points 1 to 19.

Surprisingly, it was found within the framework as contemplated herein that improved moisture resistance of styling products can be obtained by combining two constituents already known to be used in styling products.

Other properties usually required by styling products, such as high humidity curl retention, stiffness and low tack, are preserved when doing so. Such a good combination of properties was not to be expected even with knowledge of the individual components and was surprising. It was shown experimentally that by combining the two components a strong superadditive, i.e. synergistic effect was obtained with respect to moisture resistance, which manifested itself in the high humidity curl retention (HHRC) test.

As contemplated herein, the term keratinous fibers includes furs, wool and feathers, but in particular human hair.

The key constituents of the exemplified cosmetic composition are the anionic acrylate copolymer (a) and the anionic acrylate copolymer (b) which differs from the acrylate copolymer (a).

The anionic acrylate copolymer (a) is comprised of at least one (meth)acrylic acid unit (a1) and at least one (meth)acrylic acid ester unit (a2).

As contemplated herein, the copolymer (a) can be comprised of further monomer units. However, in a preferred embodiment of the invention, the copolymer (a) is comprised of only units (a1) and (a2), i.e. it consists of units derived from these monomer units.

The at least one (meth)acrylic acid unit (a1) can be a methacrylic acid or acrylic acid unit, wherein an acrylic acid unit is preferred.

The at least one (meth)acrylic acid ester unit (a2) can be a methacrylic acid ester unit or an acrylic acid ester unit, wherein an acrylic acid ester unit, in particular an acrylic acid (C1-4)-alkyl ester unit, is preferred.

The structure units (a2) quite particularly preferred are acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, methacrylic acid isopropyl ester, acrylic acid butyl ester and methacrylic acid butyl ester.

Suitable anionic acrylate copolymers (a) are available commercially with the INCI designation "acrylates copolymer". The anionic acrylate copolymer (a) Aculyn® 33A from Rohm&Haas is most preferred. In the commercially available form this has a solids content of some from about 27.5 to about 28.5 weight percent and a pH value of from about 2.1 to about 3.5.

The exemplified cosmetic compositions contain an anionic acrylate copolymer (b) as a second key constituent.

The anionic acrylate copolymer (b) is comprised of at least the following monomer units: at least one (meth)acrylic acid unit (b1), at least one (meth)acrylic acid ethyl ester unit (b2) and at least one (meth)acrylic acid ester unit (b3) which differs from the (meth)acrylic acid ethyl ester unit (b2) and has a hydrophobic group as an ester group.

As contemplated herein, the copolymer (b) can be comprised of further monomer units. But according to a preferred embodiment of the invention, the copolymer (b) is comprised of only units (b1), (b2) and (b3), i.e. it consists of units derived from these monomer units.

The at least one (meth)acrylic acid unit (b1) can be a methacrylic acid or acrylic acid unit, wherein a methacrylic acid unit is preferred.

The at least one (meth)acrylic acid ethyl ester unit (b2) can be a methacrylic acid ethyl ester unit or an acrylic acid ethyl ester unit, wherein an acrylic acid ethyl ester unit is preferred.

As contemplated herein, the at least one (meth)acrylic acid ester unit (b3) can be a (meth)acrylic acid alkyl ester unit. The alkyl group of the (meth)acrylic acid alkyl ester unit functions in a way as to control the hydrophobicity of the copolymer. The alkyl group is preferably a linear or branched alkyl group with from about 2 to about 30 carbon atoms, preferably from about 3 to about 12 carbon atoms. As contemplated herein, the hydrophobic group can also be another hydrophobic group than an alkyl group, for example an aromatic hydrocarbon ester group. A substituted or unsubstituted phenyl ester group or a substituted or unsubstituted alkylenephenyl ester group such as a benzyl ester group is an example.

The viscosity of the anionic acrylate copolymer (b) used in the cosmetic composition is preferably at most from about 60,000 to about 120,000 cPs at a solids content of 2 weight percent in a neutralized solution at 25° C.

Suitable anionic acrylate copolymers (b) are available commercially with the INCI designation "acrylates copolymer (and) water". The most preferred anionic acrylate copolymer (b) is the polymer AquaStyle® SH-100 from Ashland Inc. In the commercially available form, this has a solids content of some from about 28 to about 32 weight percent and a pH value of from about 2.1 to about 4.0.

The cosmetic composition as contemplated herein contains the acrylate copolymer (a) and acrylate copolymer (b) in the usual and suitable quantities for styling products, which can be adapted for the particular application and preparation.

For example, the exemplified composition can contain the copolymer (a) in an amount from about 0.05 to about 5.0 weight percent with reference to the total weight of the exemplified composition. Proportions of the copolymer (a) from about 0.5 to about 4.0 weight percent, in particular from about 1.0 to about 3.0 weight percent, are more preferred, in each case specified as solids content of active substance in the cosmetic composition.

The exemplified cosmetic composition contains the copolymer (b), with reference to the total weight of the cosmetic composition, for example in an amount of from about 0.05 to about 5.0 weight percent, preferably about from about 0.5 to about 4.0 weight percent, and more preferably from about 1.0 to about 3.0 weight percent, in each case specified as solids content of active substance in the cosmetic composition.

Along with the aforementioned advantages, the exemplified cosmetic compositions are also particularly distinguished by improved high humidity curl retention compared to alternative cosmetic agents. A weight ratio of polymers a) and b) from about 5:1 to about 1:5, preferably from about 3:1 to about 1:3 and in particular from about 2:1 to about 1:2 has proven particularly advantageous for the cosmetic properties of the exemplified agent.

In a particularly preferred embodiment of the present disclosure, the cosmetic composition contains the copolymer commercially available under the designation Aculyn® 33A as the anionic acrylate copolymer (a) and the copolymer commercially available under the designation AquaStyle® SH-100 as the anionic acrylate copolymer (b). Particularly good results were achieved with this combination with respect to a combination of stiffness and high humidity curl retention. This polymer combination is particularly advantageous with styling products in gel form.

Other generally required properties of styling products, such as moisture resistance and low tack are also achieved in particular with this combination, particularly with preparation as a hair gel.

The acrylate copolymers (a) and (b) are preferably used in the cosmetic composition in a form which is partially neutralized or neutralized. At least one alkanolamine is preferably used for neutralization. The alkanolamines used for alkalinization are preferably selected from primary amines with a C2-C6 alkyl base chain bearing at least one hydroxyl group. Particularly preferred alkanolamines are selected from the group comprised of 2-aminoethan-1-ol (monoethanolamine), tris(2-hydroxyethyl)-amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol and 2-amino-2-methylpropan-1,3-diol. As contemplated herein, alkanolamines which are quite particularly preferred are selected from the group of 2-aminoethan-1-ol, 2-amino-2-methylpropan-1-ol and 2-amino-2-methyl-propan-1,3-diol. Here 2-amino-2-methylpropanol has proven to be a particularly suitable for neutralization. Thus, as contemplated herein, particularly preferred cosmetic agents contain 2-amino-2-methylpropanol. The 2-amino-2-methylpropanol is preferably used in an amount which does not exceed the quantity necessary to neutralize the acrylate copolymers (a) and (b). The quantities of 2-amino-2-methylpropanol preferably used in the exemplified compositions amounts to from about 80 to 100%, from about 90 to 100% being especially preferred and in particular from about 95 to 100% of the quantity needed for complete neutralization of the acrylate copolymers (a) and (b). In a preferred embodiment, the weight fraction of 2-amino-2-methylpropanol comprises from about 0.05 to about 7.0 weight percent, preferably from about 0.05 to about 5.0 weight percent and in particular from about 0.1 to about 3.0 weight percent of the total weight of the cosmetic agent.

In summary, a preferred cosmetic composition for temporary shaping of keratinous fibers contains, with reference to its total weight:
(a) from about 0.5 to about 4.0 weight percent of at least one crosslinked copolymer (a) comprised of at least the following monomer units:
(a1) at least one (meth)acrylic acid unit
(a2) at least one (meth)acrylic acid ester unit
and
(b) from about 0.5 to about 4.0 weight percent of at least one anionic copolymer (b) comprised of at least the following monomer units:
(b1) at least one (meth)acrylic acid unit
(b2) at least one (meth)acrylic acid ethyl ester unit
(b3) at least one (meth)acrylic acid ester unit which is different from the (meth)acrylic acid ester unit (b2) and which has a hydrophobic group as an ester group.

Preferably, the cosmetic composition as contemplated herein contains one or more additional components acting as a thickening or gelling agent, which is or are supported by the acrylate copolymer (a) and (b) and likewise the film formation. Cationic, anionic, non-ionic or amphoteric polymers are examples. The weight fraction of these additional components can be comparatively low in the total weight of the cosmetic composition due to the presence of components (a) and (b) and amount to from about 0.02 to about 3 weight percent, preferably from about 0.05 to about 1.5 weight percent and even more preferably from about 0.2 to about 0.8 weight percent.

Examples are acrylamide/ammonium acrylate copolymer, acrylamides/DMAPA acrylates/methoxy PEG methacrylate copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate copolymer, acrylates/t-butylacrylamide copolymer, acrylates/C1-2 succinates/hydroxyacrylates copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/stearyl acrylate/ethylamine oxide methacrylate copolymer, acrylates/VA copolymer, acrylates/VP copolymer, adipic acid/diethylenetriamine copolymer, adipic acid/dimethylaminohydroxypropyl diethylenetriamine copolymer, adipic acid/epoxypropyl diethylenetriamine copolymer, adipic acid/isophthalic acid/neopentyl glycol/trimethylolpropane copolymer, allyl stearate/VA copolymer, aminoethylacrylate phosphate/acrylates copolymer, aminoethylpropanediol-acrylates/acrylamide copolymer, aminoethylpropanediol-AMPD-acrylates/diacetoneacrylamide copolymer, ammonium VA/acrylates copolymer, AMPD-acrylates/diacetoneacrylamide copolymer, AMP-acrylates/allyl methacrylate copolymer, AMP-acrylates/C1-18 alkyl acrylates/C1-8 alkyl acrylamide copolymer, AMP-acrylates/diacetoneacrylamide copolymer, AMP-acrylates/dimethylaminoethylmethacrylate copolymer, *bacillus*/rice bran extract/soybean extract ferment filtrate, bis-butyloxyamodimethicone/PEG-60 copolymer, butyl acrylate/ethylhexyl methacrylate copolymer, butyl acrylate/hydroxypropyl dimethicone acrylate copolymer, butylated PVP, butyl ester of ethylene/MA copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, dimethicone crosspolymer, diphenyl amodimethicone, ethyl ester of PVM/MA copolymer, hydrolyzed wheat protein/PVP crosspolymer, isobutylene/ethylmaleimide/hydroxyethylmaleimide copolymer, isobutylene/MA copolymer, isobutylmethacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, MEA sulfite, methacrylic acid/sodium acrylamidomethyl propane sulfonate copolymer, methacryloyl ethyl betaine/acrylates copolymer, octylacrylamide/acrylates/butylaminoethyl methacrylate copolymer, PEG/PPG-25/25 dimethicone/acrylates copolymer, PEG-8/SMDI copolymer, polyacrylamide, polyacrylate-6, polybeta-alanine/glutaric acid crosspolymer, polybutylene terephthalate, polyester-1, polyethylacrylate, polyethylene terephthalate, polymethacryloyl ethyl betaine, polypentaerythrityl terephthalate, polyperfluoroperhydrophenanthrene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-24, polyquaternium-27, polyquaternium-28, polyquaternium-29, polyquaternium-30, polyquaternium-31, polyquaternium-32, polyquaternium-33, polyquaternium-34, polyquaternium-35, polyquaternium-36, polyquaternium-37, polyquaternium-39, polyquaternium-45, polyquaternium-46, polyquaternium-47, polyquaternium-48, polyquaternium-49, polyquaternium-50, polyquaternium-55, polyquaternium-56, polysilicone-9, polyurethane-1, polyurethane-6, polyurethane-10, polyvinyl acetate, polyvinyl butyral, polyvinylcaprolactam, polyvinylformamide, polyvinyl imidazolinium acetate, polyvinyl methyl ether, potassium butyl ester of PVM/MA copolymer, potassium ethyl ester of PVM/MA copolymer, PPG-70 polyglyceryl-10 ether, PPG-12/SMDI copolymer, PPG-51/SMDI copolymer, PPG-10 sorbitol, PVM/MA copolymer, PVP, PVP/VA/itaconic acid copolymer, PVP/VA/vinyl propionate copolymer, rhizobian gum, rosin acrylate, shellac, sodium butyl ester of PVM/MA copolymer, sodium ethyl ester of PVM/MA copolymer, sodium polyacrylate, Sterculia urens gum, terephthalic acid/isophthalic acid/sodium isophthalic acid sulfonate/glycol copolymer, trimethylolpropane triacrylate, trimethylsiloxysilylcarbamoyl pullulan, VA/crotonates copolymer, VA/crotonates/methacryloxybenzophenone-1 copolymer, VA/crotonates/vinyl neodecanoate copolymer, VA/crotonates/vinyl propionate copolymer, VA/DBM copolymer, VA/vinyl butyl benzoate/crotonates copolymer, vinylamine/vinyl alcohol copolymer, vinyl caprolactam/VP/dimethylaminoethyl methacrylate copolymer, VP/acrylates/lauryl methacrylate copolymer, VP/dimethylaminoethylmethacrylate copolymer, VP/DMAPA acrylates copolymer, VP/hexadecene copolymer, VP/VA copolymer, VP/vinyl caprolactam/DMAPA acrylates copolymer, yeast palmitate and styrene/VP copolymer.

Examples of non-ionic polymers are:

Vinyl pyrrolidone/vinyl ester copolymers as sold under the trademark Luviskol (BASF), for example. Luviskol VA 64 and Luviskol VA 73, each vinyl pyrrolidone/vinyl acetate copolymers, are preferred non-ionic polymers.

Cellulose ethers such as hydroxypropyl cellulose, hydroxyethyl cellulose and methylhydroxypropyl cellulose as sold, for example, under the trademark Culminalund Benecel (from AQUALON).

Shellac.

Polyvinyl pyrrolidones as sold, for example, under the trademark Luviskol (from BASF).

Siloxanes. These siloxanes can be water-soluble as well as insoluble in water. Both volatile and non-volatile siloxanes are suitable, wherein non-volatile siloxanes are understood as compounds whose boiling point is above 200° C. at normal pressure. Preferred siloxanes are polydialkylsiloxanes such as polydimethylsiloxane, polyalkylarylsiloxanes such as polyphenylmethylsiloxane, ethoxylated polydialkylsiloxanes and polydialkylsiloxanes containing amine and/or hydroxyl groups.

Glycosidic substituted silicone.

A homopolyacrylic acid (INCI: carbomer) available in various implementations commercially as Carbopol® is preferred and also acts as a gelling agent. The carbomer is preferably contained in a proportion of from about 0.02 to about 3 weight percent, preferably from about 0.05 to about 1.5 weight percent and more preferably from about 0.2 to about 0.8 weight percent with reference to the total weight of the cosmetic composition.

As contemplated herein, due to their cosmetic effect in combination with the copolymers a) and b) preferred polymers which form films are, in particular, the polyvinyl pyrrolidones (INCI designation; PVPs) and the vinyl pyrrolidone/vinyl acetate copolymers (INCI designation: VP/VA copolymers), with the weight fraction of these polymers preferably limited to quantities between about 1.0 and about 10 weight percent. Particularly preferable exemplified cosmetic compositions are therefore characterized in that they also contain from about 1.0 to about 10 weight percent polyvinyl pyrrolidone and/or vinyl pyrrolidone/vinyl acetate copolymer, preferably polyvinyl pyrrolidone, with reference to their total weight. Particularly preferred cosmetic agents have a weight fraction of polyvinyl pyrrolidone and/or vinyl pyrrolidone/vinyl acetate copolymer c) of from about 2.0 to about 8.5 weight percent, preferably of from about 3.0 to about 7.0 weight percent, of the total weight of the cosmetic agent.

The exemplified cosmetic composition can also contain usual styling product materials. Additional care substances are to be mentioned in particular as further suitable auxiliary and additive materials.

For example, the medium can contain a protein hydrolysate and/or one of its derivatives as a care substance. Protein hydrolysates are product mixtures obtained by acid-, base- or enzyme-catalyzed degradation of proteins. As contemplated herein, the term protein hydrolysates are also understood to be complete hydrolysates and individual amino acids and their derivates as well as mixtures of various amino acids. The molecular weight of the exemplary replaceable protein hydrolysates is between about 75, the molecular weight of glycine, and about 200,000, preferably being between about 75 and about 50,000 and quite particularly preferred between about 75 and about 20,000 daltons.

Furthermore, the exemplified medium can contain at least one vitamin, a provitamin, a vitamin precursor and/or one of its derivates as a care substance. As contemplated herein preferred vitamins, provitamins and vitamin precursors for this are usually classified in the groups A, B, C, E, F and H.

As with the addition of glycerine and/or propylene glycol, the addition of panthenol increases the flexibility of the polymer film formed during application of the exemplified medium.

Furthermore, the exemplified medium can contain at least one plant extract as well as mono- and/or oligosaccharides and/or lipids as a care substance.

Oil particles are also suitable as a care substance. Natural and synthetic oil particles include, for example, vegetable oils, liquid paraffins, isoparaffins and synthetic hydrocarbons as well as di-n-alkyl ethers with between 12 to 36 carbon atoms altogether, in particular 12 to 24 carbon atoms. Preferred exemplified cosmetic agents contain at least one oil particle, preferably at least one oil particle from the group of silicone oils. The group of silicone oils particularly includes dimethicones, which also include cyclomethicones, aminofunctional silicones and dimethiconols. The dimethicones can be linear as well as branched and also cyclic or cyclic and branched. Suitable silicone oils or silicone gums are in particular dialkyl and alkylaryl siloxanes such as polydimethylsiloxane and polymethylphenylsiloxane as well as their alkoxylated, quaternized or also anionic derivates. Cyclic and linear polydialkylsiloxanes are preferred, as are their alkoxylated and/or aminated derivatives, dihydroxypolydimethylsiloxanes and polyphenylalkylsiloxanes.

Further preferred oil particles for care are ester oils, i.e. esters of C6-C30 fatty acids with C2-C30 fatty alcohols, preferably monoesters of fatty acids with alcohols with 2 to 24 carbon atoms, such as isopropyl myristate (Rilanit® IPM) for example, isononanoic acid-C16-18 alkyl ester (Cetiol® SN), 2-ethylhexyl palmitate (Cegesoft® 24), stearic acid 2-ethylhexyl ester (Cetiol® 868), cetyl oleate, glycerine tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN) and decyl oleate (Cetiol® V).

Also suitable as care substances are dicarboxylic acid esters, symmetric, asymmetric or cyclic esters of carboxylic acids with fatty alcohols, triglycerides of saturated and/or unsaturated linear and/or branched fatty acids with glycerine or partial glycerides of fatty acids, which are to be understood as monoglycerides, diglycerides and their technical mixtures.

Furthermore, emulsifiers and/or surface-active media are preferably contained in the exemplified composition. PEG derivates of hydrogenated castor oil, available under the designation PEG hydrogenated castor oil, for example PEG-30 hydrogenated castor oil, PEG-33 hydrogenated castor oil, PEG-35 hydrogenated castor oil, PEG-36 hydrogenated castor oil or PEG-40 hydrogenated castor oil, are preferred. As contemplated herein, the use of PEG-40 hydrogenated castor oil is preferred. This is preferably contained in an amount of from about 0.05 to about 1.5 weight percent, more preferably from about 0.1 to about 1.0 weight percent as well as preferably from about 0.2 to about 0.8 weight percent or from about 0.3 to about 0.6 weight percent.

The exemplified cosmetic products contain the ingredients and/or active substances in a cosmetically acceptable medium.

Preferred cosmetically acceptable media are aqueous, alcoholic or aqueous/alcoholic media with preferably at least about 10 weight percent water based on the total weight of the medium.

It is particularly preferred that the exemplified cosmetic agent contain water, in particular in the amount such that the cosmetic agent contains at least about 10 weight percent water, in particular at least about 20.0 weight percent, and most preferably at least 40 weight percent based on the total weight of the medium. Quite particularly preferred cosmetic agents have a water fraction between about 50 and about 95 weight percent based on their total weight, preferably between about 60 and about 90 weight percent and in particular between about 65 and about 85 weight percent.

For cosmetic purposes in particular typically used lower alcohols with 1 to 4 carbon atoms can be contained as alcohols, for example ethanol and isopropanol.

Examples of water-soluble solvents as co-solvents are glycerine and/or ethylene glycol and/or 1,2-propylene glycol in an amount from about 0 to about 30 weight percent with reference to the entire medium.

Tabular Overview

The composition of some preferred cosmetic agents can be found in the tables below. (Data in weight percent refer to the total weight of the cosmetic agent if not otherwise indicated.)

|  | Formula 1 | Formula 2 | Formula 3 | Formula 4 | Formula 5 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| Misc | add 100 | add 100 | add 100 | add 100 | add 100 |

|  | Formula 1a | Formula 2a | Formula 3a | Formula 4a | Formula 5a |
|---|---|---|---|---|---|
| Copolymer a): acrylates copolymer | 0.05 to 5.0 | 0.5 to 4.0 | 0.5 to 4.0 | 1.0 to 3.0 | 1.0 to 3.0 |
| Copolymer b): Acrylate copolymer (and) water | 0.05 to 5.0 | 0.05 to 5.0 | 0.5 to 4.0 | 0.5 to 4.0 | 1.0 to 3.0 |
| Misc | add 100 | add 100 | add 100 | add 100 | add 100 |

|  | Formula 1b | Formula 2b | Formula 3b | Formula 4b | Formula 5b |
|---|---|---|---|---|---|
| Copolymer a): Aculyn ® 33A (data for solids content) | 0.05 to 5.0 | 0.5 to 4.0 | 0.5 to 4.0 | 1.0 to 3.0 | 1.0 to 3.0 |
| Copolymer b): AquaStyle ® SH-100 (data for solids content) | 0.05 to 5.0 | 0.05 to 5.0 | 0.5 to 4.0 | 0.5 to 4.0 | 1.0 to 3.0 |
| Misc | add 100 | add 100 | add 100 | add 100 | add 100 |

|  | Formula 6 | Formula 7 | Formula 8 | Formula 9 | Formula 10 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| Polyvinyl pyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 6a | Formula 7a | Formula 8a | Formula 9a | Formula 10a |
| --- | --- | --- | --- | --- | --- |
| Copolymer a): acrylates copolymer | 0.05 to 5.0 | 0.5 to 4.0 | 0.5 to 4.0 | 1.0 to 3.0 | 1.0 to 3.0 |
| Copolymer b): acrylates copolymer (and) water | 0.05 to 5.0 | 0.05 to 5.0 | 0.5 to 4.0 | 0.5 to 4.0 | 1.0 to 3.0 |
| Polyvinyl pyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 6b | Formula 7b | Formula 8b | Formula 9b | Formula 10b |
| --- | --- | --- | --- | --- | --- |
| Copolymer a): Aculyn ® 33A (data for solids content) | 0.05 to 5.0 | 0.5 to 4.0 | 0.5 to 4.0 | 1.0 to 3.0 | 1.0 to 3.0 |
| Copolymer b): AquaStyle ® SH-100 (data for solids content) | 0.05 to 5.0 | 0.05 to 5.0 | 0.5 to 4.0 | 0.5 to 4.0 | 1.0 to 3.0 |
| Polyvinyl pyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 11 | Formula 12 | Formula 13 | Formula 14 | Formula 15 |
| --- | --- | --- | --- | --- | --- |
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| Vinyl pyrrolidone/vinyl acetate Copolymer | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 11a | Formula 12a | Formula 13a | Formula 14a | Formula 15a |
| --- | --- | --- | --- | --- | --- |
| Copolymer a): acrylates copolymer | 0.05 to 5.0 | 0.5 to 4.0 | 0.5 to 4.0 | 1.0 to 3.0 | 1.0 to 3.0 |
| Copolymer b): acrylates copolymer (and) water | 0.05 to 5.0 | 0.05 to 5.0 | 0.5 to 4.0 | 0.5 to 4.0 | 1.0 to 3.0 |
| Vinyl pyrrolidone/vinyl acetate Copolymer | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 11b | Formula 12b | Formula 13b | Formula 14b | Formula 15b |
| --- | --- | --- | --- | --- | --- |
| Copolymer a): Aculyn ® 33A (data for solids content) | 0.05 to 5.0 | 0.5 to 4.0 | 0.5 to 4.0 | 1.0 to 3.0 | 1.0 to 3.0 |
| Copolymer b): AquaStyle ® SH-100 (data for solids content) | 0.05 to 5.0 | 0.05 to 5.0 | 0.5 to 4.0 | 0.5 to 4.0 | 1.0 to 3.0 |
| Vinyl pyrrolidone/vinyl acetate Copolymer | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 16 | Formula 17 | Formula 18 | Formula 19 | Formula 20 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

|  | Formula 16a | Formula 17a | Formula 18a | Formula 19a | Formula 20a |
|---|---|---|---|---|---|
| Copolymer a): acrylates copolymer | 0.05 to 5.0 | 0.5 to 4.0 | 0.5 to 4.0 | 1.0 to 3.0 | 1.0 to 3.0 |
| Copolymer b): acrylates copolymer (and) water | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

|  | Formula 16b | Formula 17b | Formula 18b | Formula 19b | Formula 20b |
|---|---|---|---|---|---|
| Copolymer a): Aculyn ® 33A (data for solids content) | 0.05 to 5.0 | 0.5 to 4.0 | 0.5 to 4.0 | 1.0 to 3.0 | 1.0 to 3.0 |
| Copolymer b): AquaStyle ® SH-100 (data for solids content) | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

|  | Formula 21 | Formula 22 | Formula 23 | Formula 24 | Formula 25 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

|  | Formula 21a | Formula 22a | Formula 23a | Formula 24a | Formula 25a |
|---|---|---|---|---|---|
| Copolymer a): acrylates copolymer | 0.05 to 5.0 | 0.5 to 4.0 | 0.5 to 4.0 | 1.0 to 3.0 | 1.0 to 3.0 |
| Copolymer b): acrylates copolymer (and) water | 0.05 to 5.0 | 0.05 to 5.0 | 0.5 to 4.0 | 0.5 to 4.0 | 1.0 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

|  | Formula 21b | Formula 22b | Formula 23b | Formula 24b | Formula 25b |
|---|---|---|---|---|---|
| Copolymer a): Aculyn ® 33A (data for solids content) | 0.05 to 5.0 | 0.5 to 4.0 | 0.5 to 4.0 | 1.0 to 3.0 | 1.0 to 3.0 |
| Copolymer b): AquaStyle ® SH-100 (data for solids content) | 0.05 to 5.0 | 0.05 to 5.0 | 0.5 to 4.0 | 0.5 to 4.0 | 1.0 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

|  | Formula 26 | Formula 27 | Formula 28 | Formula 29 | Formula 30 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| Water | 50 to 95 | 50 to 95 | 60 to 90 | 60 to 90 | 65 to 85 |
| Misc | add 100 | add 100 | add 100 | add 100 | add 100 |

|  | Formula 26a | Formula 27a | Formula 28a | Formula 29a | Formula 30a |
|---|---|---|---|---|---|
| Copolymer a): acrylates copolymer | 0.05 to 5.0 | 0.5 to 4.0 | 0.5 to 4.0 | 1.0 to 3.0 | 1.0 to 3.0 |
| Copolymer b): acrylates copolymer (and) water | 0.05 to 5.0 | 0.05 to 5.0 | 0.5 to 4.0 | 0.5 to 4.0 | 1.0 to 3.0 |
| Water | 50 to 95 | 50 to 95 | 60 to 90 | 60 to 90 | 65 to 85 |
| Misc | add 100 | add 100 | add 100 | add 100 | add 100 |

|  | Formula 26b | Formula 27b | Formula 28b | Formula 29b | Formula 30b |
|---|---|---|---|---|---|
| Copolymer a): Aculyn® 33A (data for solids content) | 0.05 to 5.0 | 0.5 to 4.0 | 0.5 to 4.0 | 1.0 to 3.0 | 1.0 to 3.0 |
| Copolymer b): AquaStyle® SH-100 (data for solids content) | 0.05 to 5.0 | 0.05 to 5.0 | 0.5 to 4.0 | 0.5 to 4.0 | 1.0 to 3.0 |
| Water | 50 to 95 | 50 to 95 | 60 to 90 | 60 to 90 | 65 to 85 |
| Misc | add 100 | add 100 | add 100 | add 100 | add 100 |

|  | Formula 31 | Formula 32 | Formula 33 | Formula 34 | Formula 35 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| Polyvinyl pyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 31a | Formula 32a | Formula 33a | Formula 34a | Formula 35a |
|---|---|---|---|---|---|
| Copolymer a): acrylates copolymer | 0.05 to 5.0 | 0.5 to 4.0 | 0.5 to 4.0 | 1.0 to 3.0 | 1.0 to 3.0 |
| Copolymer b): acrylates copolymer (and) water | 0.05 to 5.0 | 0.05 to 5.0 | 0.5 to 4.0 | 0.5 to 4.0 | 1.0 to 3.0 |
| Polyvinyl pyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 31b | Formula 32b | Formula 33b | Formula 34b | Formula 35b |
|---|---|---|---|---|---|
| Copolymer a): Aculyn® 33A (data for solids content) | 0.05 to 5.0 | 0.5 to 4.0 | 0.5 to 4.0 | 1.0 to 3.0 | 1.0 to 3.0 |
| Copolymer b): AquaStyle® SH-100 (data for solids content) | 0.05 to 5.0 | 0.05 to 5.0 | 0.5 to 4.0 | 0.5 to 4.0 | 1.0 to 3.0 |
| Polyvinyl pyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36 | Formula 37 | Formula 38 | Formula 39 | Formula 40 |
| --- | --- | --- | --- | --- | --- |
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| Vinyl pyrrolidone/vinyl acetate Copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36a | Formula 37a | Formula 38a | Formula 39a | Formula 40a |
| --- | --- | --- | --- | --- | --- |
| Copolymer a): acrylates copolymer | 0.05 to 5.0 | 0.5 to 4.0 | 0.5 to 4.0 | 1.0 to 3.0 | 1.0 to 3.0 |
| Copolymer b): acrylates copolymer (and) water | 0.05 to 5.0 | 0.05 to 5.0 | 0.5 to 4.0 | 0.5 to 4.0 | 1.0 to 3.0 |
| Vinyl pyrrolidone/vinyl acetate Copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36b | Formula 37b | Formula 38b | Formula 39b | Formula 40b |
| --- | --- | --- | --- | --- | --- |
| Copolymer a): Aculyn ® 33A (data for solids content) | 0.05 to 5.0 | 0.5 to 4.0 | 0.5 to 4.0 | 1.0 to 3.0 | 1.0 to 3.0 |
| Copolymer b): AquaStyle ® SH-100 (data for solids content) | 0.05 to 5.0 | 0.05 to 5.0 | 0.5 to 4.0 | 0.5 to 4.0 | 1.0 to 3.0 |
| Vinyl pyrrolidone/vinyl acetate Copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 41 | Formula 42 | Formula 43 | Formula 44 | Formula 45 |
| --- | --- | --- | --- | --- | --- |
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 41a | Formula 42a | Formula 43a | Formula 44a | Formula 45a |
|---|---|---|---|---|---|
| Copolymer a) acrylates copolymer | 0.05 to 5.0 | 0.5 to 4.0 | 0.5 to 4.0 | 1.0 to 3.0 | 1.0 to 3.0 |
| Copolymer b) acrylates copolymer (and) water | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 41b | Formula 42b | Formula 43b | Formula 44b | Formula 45b |
|---|---|---|---|---|---|
| Copolymer a): Aculyn ® 33A (data for solids content) | 0.05 to 5.0 | 0.5 to 4.0 | 0.5 to 4.0 | 1.0 to 3.0 | 1.0 to 3.0 |
| Copolymer b): AquaStyle ® SH-100 (data for solids content) | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 46 | Formula 47 | Formula 48 | Formula 49 | Formula 50 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

|  | Formula 46a | Formula 47a | Formula 48a | Formula 49a | Formula 50a |
|---|---|---|---|---|---|
| Copolymer a): acrylates copolymer | 0.05 to 5.0 | 0.5 to 4.0 | 0.5 to 4.0 | 1.0 to 3.0 | 1.0 to 3.0 |
| Copolymer b): acrylates copolymer (and) water | 0.05 to 5.0 | 0.05 to 5.0 | 0.5 to 4.0 | 0.5 to 4.0 | 1.0 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

|  | Formula 46b | Formula 47b | Formula 48b | Formula 49b | Formula 50b |
|---|---|---|---|---|---|
| Copolymer a): Aculyn ® 33A (data for solids content) | 0.05 to 5.0 | 0.5 to 4.0 | 0.5 to 4.0 | 1.0 to 3.0 | 1.0 to 3.0 |
| Copolymer b): AquaStyle ® SH-100 (data for solids content) | 0.05 to 5.0 | 0.05 to 5.0 | 0.5 to 4.0 | 0.5 to 4.0 | 1.0 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

As contemplated herein, "misc" is to be understood as a cosmetic medium, in particular (if not listed separately) water and possibly other usual styling product constituents.

The cosmetic composition of the present disclosure can be prepared in the usual forms for temporary shaping of hair, for example as a hair gel, hairspray, hair foam or hair wax. Preparation as a hair gel is preferred.

Both hair foams and hairsprays require the presence of propellants. However, as contemplated herein preferably no hydrocarbons or only low quantities of hydrocarbons are to be used. Propane, propane/butane mixtures and dimethyl ether are particularly suitable propellants as contemplated herein.

The present disclosure also relates to the use of exemplified cosmetic compositions for temporary shaping of keratinous fibers, in particular human hair and a method for temporary shaping of keratinous fibers, in particular human hair, in which the exemplified cosmetic composition is applied to keratinous fibers.

A further subject of this patent application is the use of an exemplified cosmetic composition to improve the moisture resistance of temporarily shaped keratinous fibers.

EXAMPLES

The following hair gels were made:

| Component/raw material | INCI designation or chemical name | V1 | V2 | E1 |
|---|---|---|---|---|
| Aculyn ® A33 [1] | Acrylates copolymer | 3.58 | — | 1.79 |
| AquaStyle SH-100 [2] | Acrylates copolymer (and) water | — | 3.3 | 1.65 |
| AMP-ULTRA PC 2000 | Aminomethyl propanol | 0.24 | 0.3 | 0.27 |
| Water | | 96.18 | 96.4 | 96.29 |
| Total | | 100 | 100 | 100 |

[1] 28 weight percent active substance in water
[2] 30 weight percent active substance in water The quantity information in the table is given as the weight percent of the respective raw material with reference to the entire composition. The polymer content in each of the compositions V1, V2 and E1 comprised 1.0 weight percent.

The moisture resistance (the mean value for the determination with 5 hair strands in each case) was measured for the styling product obtained using a high humidity curl retention (HHCR) test for 6 hours on new Kerling hair strands.

| | V1 | V2 | E1 |
|---|---|---|---|
| HHCR | 63% | 51% | 71% |

The exemplified polymer combination E1 consequently exhibited a clearly superadditive, synergistic effect with reference to moisture resistance.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition for temporary shaping of keratinous fibers, the cosmetic composition consisting of:
   an acrylate copolymer (a) which consists of the following monomer units;
   at least one (meth)acrylic acid unit, and
   at least one (meth)acrylic acid ester unit;
   an anionic acrylate copolymer (b) consisting of the following monomer units;
   at least methacrylic acid unit,
   at least one ethyl acrylate unit, and
   at least one (meth)acrylic acid alkyl ester;
   at least one alkanolamine;
   water in a proportion of at least 50% by weight with respect to the total weight of the cosmetic composition; and
   optionally, at least one polymer (c) chosen from polyvinyl pyrrolidone, vinyl pyrrolidone/vinyl acetate copolymer, or homopolyacrylic acid.

2. The cosmetic composition according to claim 1, wherein the composition comprises the copolymer (a) in a proportion of from about 0.5 to about 4.0 weight percent with reference to the total weight of the cosmetic composition.

3. The cosmetic composition according to claim 1, wherein the composition comprises the anionic acrylate copolymer (b) in a proportion of from about 0.5 to about 4.0 weight percent with reference to the total weight of the cosmetic composition.

4. The cosmetic composition according to claim 1, wherein the composition is present as a hair gel, hairspray, hair foam or hair wax.

5. The cosmetic composition according to claim 1, wherein the cosmetic composition is utilized for temporary shaping of keratinous fibers.

6. A method for temporary shaping of keratinous fibers, the method comprising applying the cosmetic composition according to claim 1 to keratinous fibers.

7. The cosmetic composition according to claim 1, wherein the anionic acrylate copolymer (b) has a viscosity of from about 60,000 to about 120,000 cPs at a solids content of 2 weight percent in an aqueous neutralized solution at 25° C.

8. The cosmetic composition according to claim 1, wherein the at least one polymer (c) is present in an amount of from about 1.0 to about 10 weight percent with reference to the total weight of the cosmetic composition.

9. The cosmetic composition according to claim 8, wherein the at least one polymer (c) comprises polyvinyl pyrrolidone.

10. The cosmetic composition according to claim 1, wherein the at least one alkanolamine comprises 2-aminoethan-1-ol, 2-amino-2-methylpropan-1-ol, 2-amino-2-methyl-propan-1,3-diol, or combinations thereof.

11. The cosmetic composition of claim 1, wherein the at least one copolymer (a) consists of the at least one (meth) acrylic acid unit and at least one acrylic acid (C1-4)-alkyl ester unit.

12. The cosmetic composition of claim 11, wherein the at least one copolymer (b) consists of the following monomer units:
- (b1) at least one acrylic acid unit,
- (b2) at least one ethyl acrylate unit, and
- (b3) at least one (meth)acrylic acid alkyl ester unit which is different from the (meth)acrylic acid ester unit (b2) and which has a hydrophobic group as an ester group.

13. The cosmetic composition of claim 12, wherein the composition comprises the copolymer (a) in a proportion of from about 0.5% to about 4.0% by weight with respect to the total weight of the cosmetic composition.

14. The cosmetic composition of claim 13, wherein the composition comprises the copolymer (b) in a proportion of from about 0.5 to about 4.0% by weight with respect to the total weight of the cosmetic composition.

15. The cosmetic composition of claim 14, wherein copolymer (a) is crosslinked.

\* \* \* \* \*